US00PP14062P39

(12) United States Plant Patent
Amorao et al.

(10) Patent No.: US PP14,062 P3
(45) Date of Patent: Aug. 12, 2003

(54) STRAWBERRY PLANT NAMED 'DRISCOLL VENICE'

(75) Inventors: Amado Q. Amorao, Camarillo, CA (US); Arnoldo Solis, Jr., Oxnard, CA (US); Michael Ferguson, Chatsworth, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/975,824

(22) Filed: Oct. 12, 2001

(65) Prior Publication Data

US 2002/0129410 P1 Sep. 12, 2002

(51) Int. Cl.[7] ..... A01H 5/00

(52) U.S. Cl. ..... Plt./209

(58) Field of Search ..... Plt./209, 208

*Primary Examiner*—Bruce R. Campell
*Assistant Examiner*—Susan B. McCormick
(74) *Attorney, Agent, or Firm*—Pennie & Edmonds, LLP

(57) ABSTRACT

This invention relates to a new and distinct variety of strawberry named 'Driscoll Venice'. The variety is similar to the varieties 'Coronado' and 'San Miguel'. The variety is distinguished from 'Coronado' and 'San Miguel', in particular, the plant is medium dense, shape of terminal leaflet is obtuse, petiole pubescence is dense, predominant fruit shape is cordate, insertion of achenes is level with surface, and fruit acidity is weak.

4 Drawing Sheets

Latin name of the genus and species of the plant claimed: The variety is botanically identified as *Fragraria×ananassa.*

BACKGROUND OF THE INVENTION

The new variety originated as a result of a controlled cross between the strawberry plants 'Ana Maria' (U.S. Plant Pat. No. 11,035) and 'Balboa' (U.S. Plant Pat. No. 9,130) in an ongoing breeding program, and was discovered as a seedling in a controlled breeding plot in Ventura County, Calif. in February, 1996. The original seedling of the new cultivar was asexually propagated by stolons in McArthur, Shasta County, Calif. propagules were transplanted to a controlled breeding plot in Ventura County, Calif. where the variety was identified and selected for further evaluation. 'Driscoll Venice' was subsequently asexually propagated and underwent further testing in Ventura County, Calif. for six years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'Driscoll Venice'. The variety is botanically identified as *Fragaria×ananassa.* The new variety is distinguished from other varieties by a number of characteristics as set forth in Tables 1–4.

COMPARISON TO SIMILAR VARIETIES

The varieties which we believe to be similar to 'Driscoll Venice' from those known to us are 'Coronado' (U.S. Plant Pat. No. 10,221) and 'San Miguel' (U.S. Plant Pat. No. 10,642). There are several characteristics of the new variety that are different from, or not possessed by 'Coronado' and 'San Miguel'. The new variety is medium dense, shape of terminal leaflet is obtuse, petiole pubescence is dense, predominant fruit shape is cordate, insertion of achenes is level with surface, and fruit acidity is weak.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
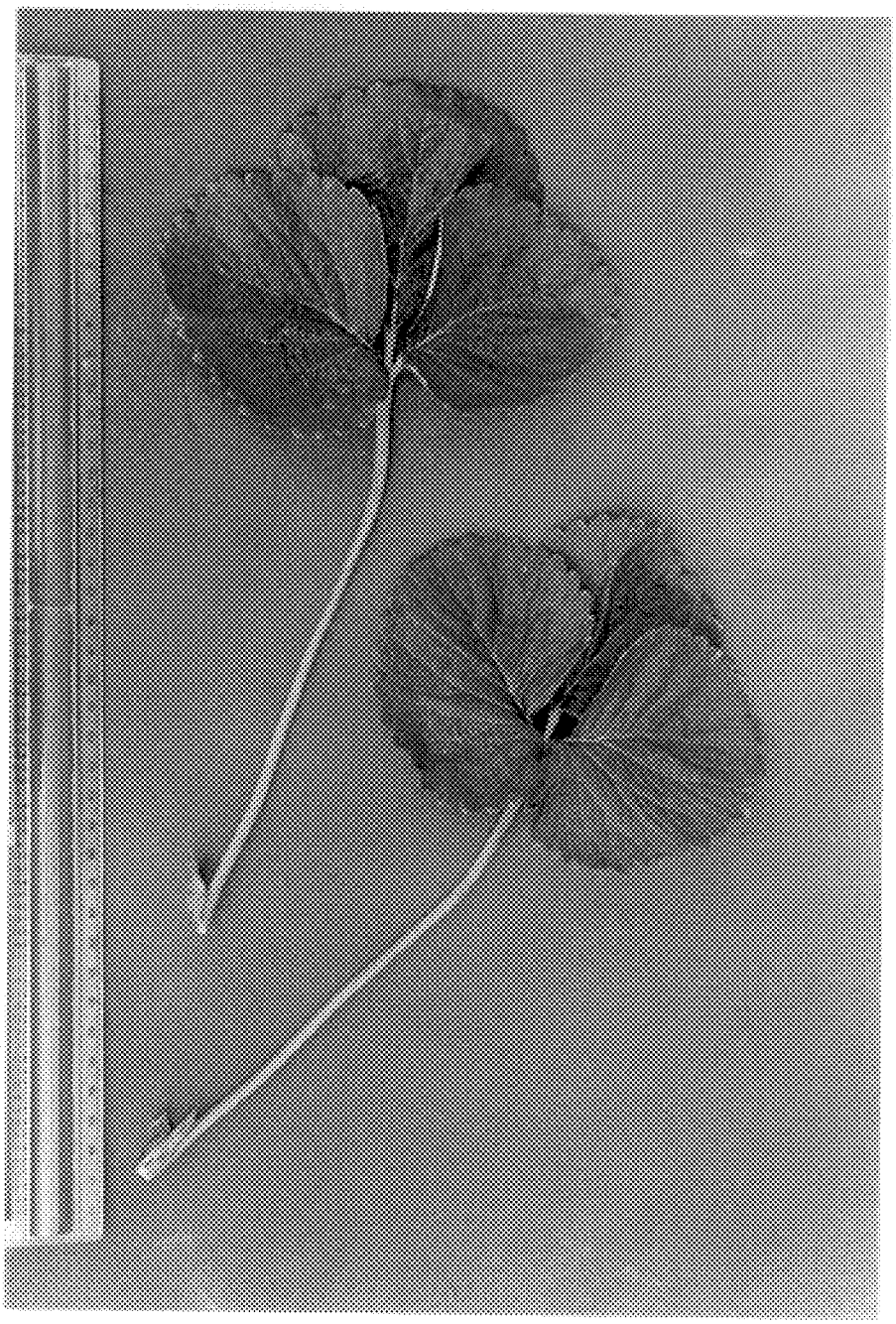
FIG. 1 shows the leaves of the plant.
Figure 2:
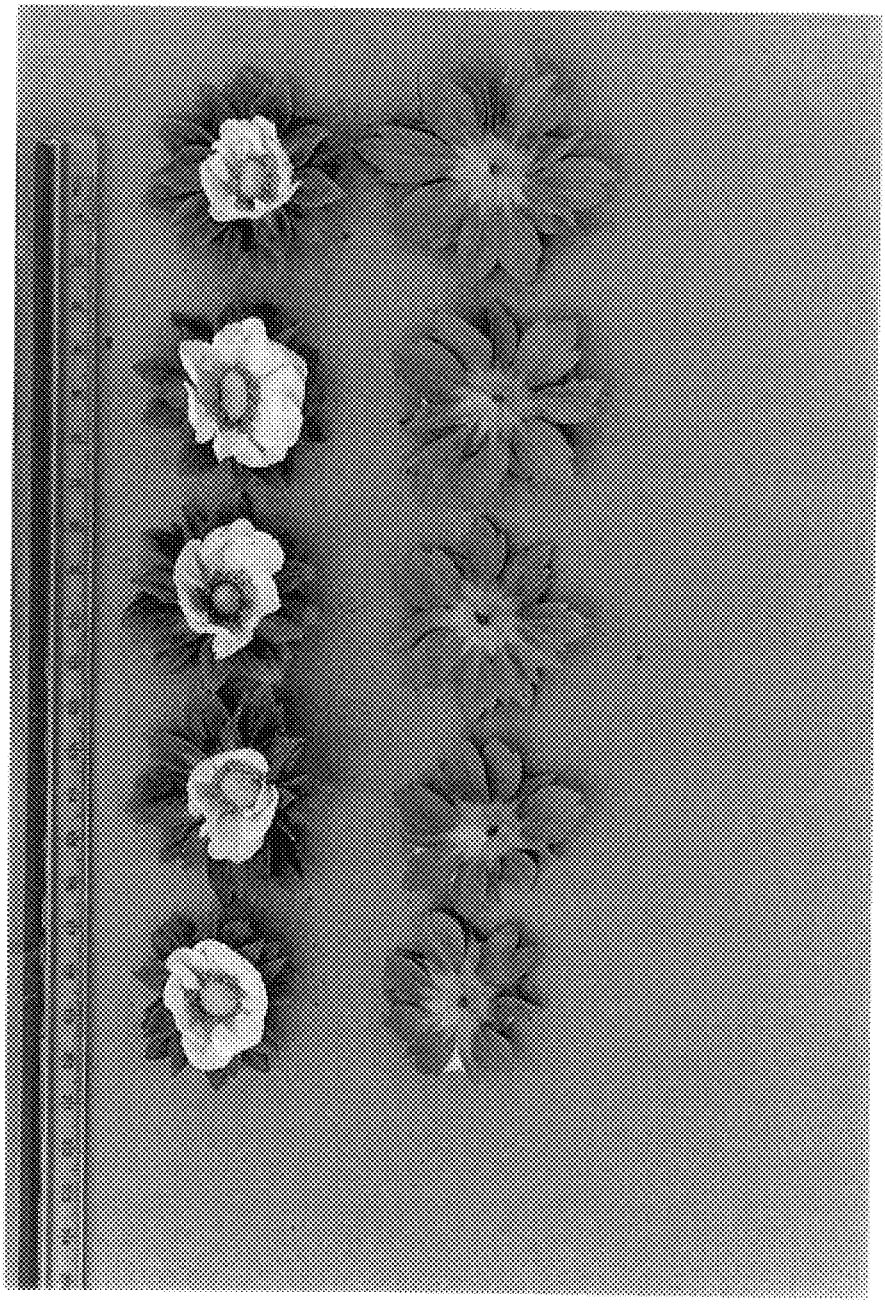
FIG. 2 shows the upper side and the under side of the flowers.
Figure 3:
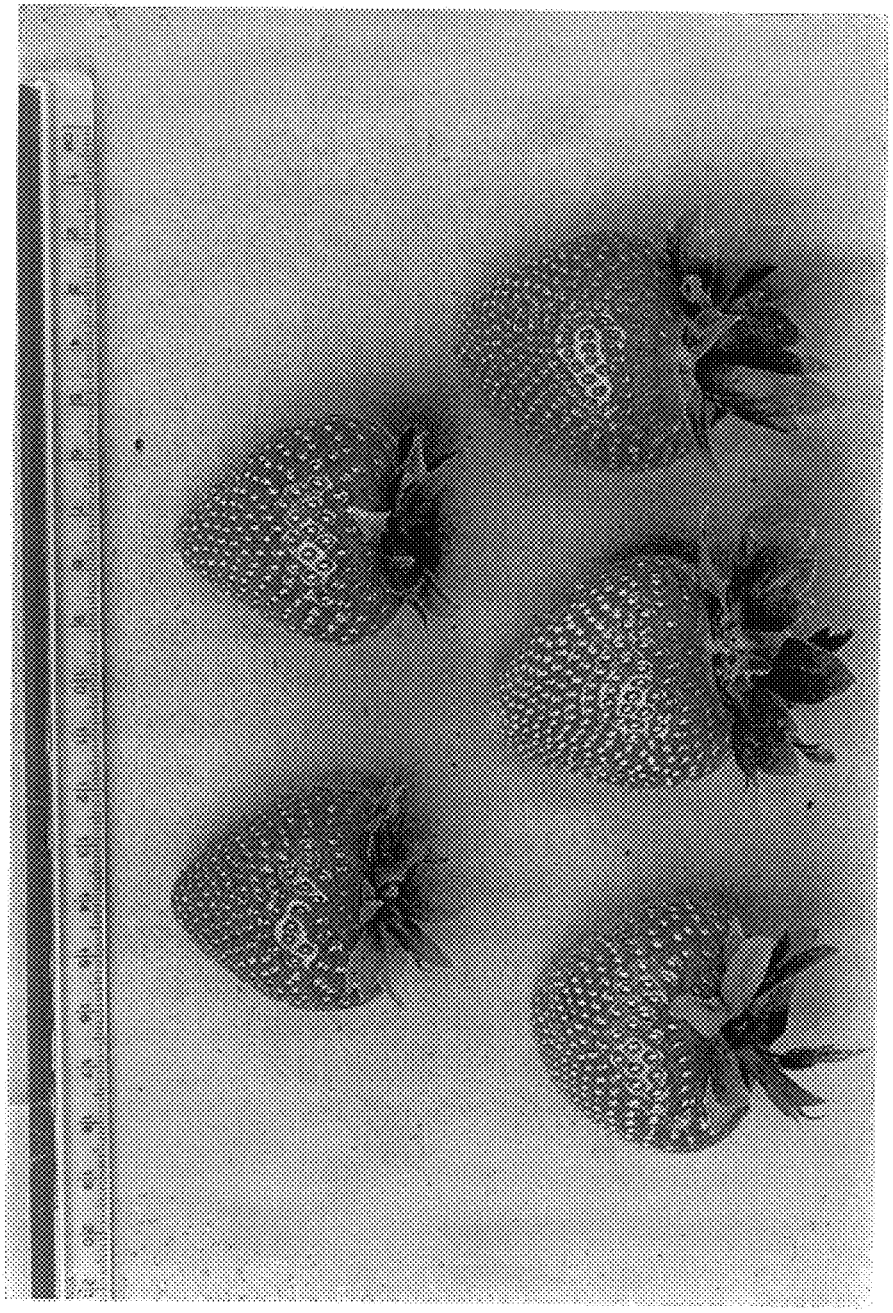
FIG. 3 shows a close-up of the fruit.
Figure 4:
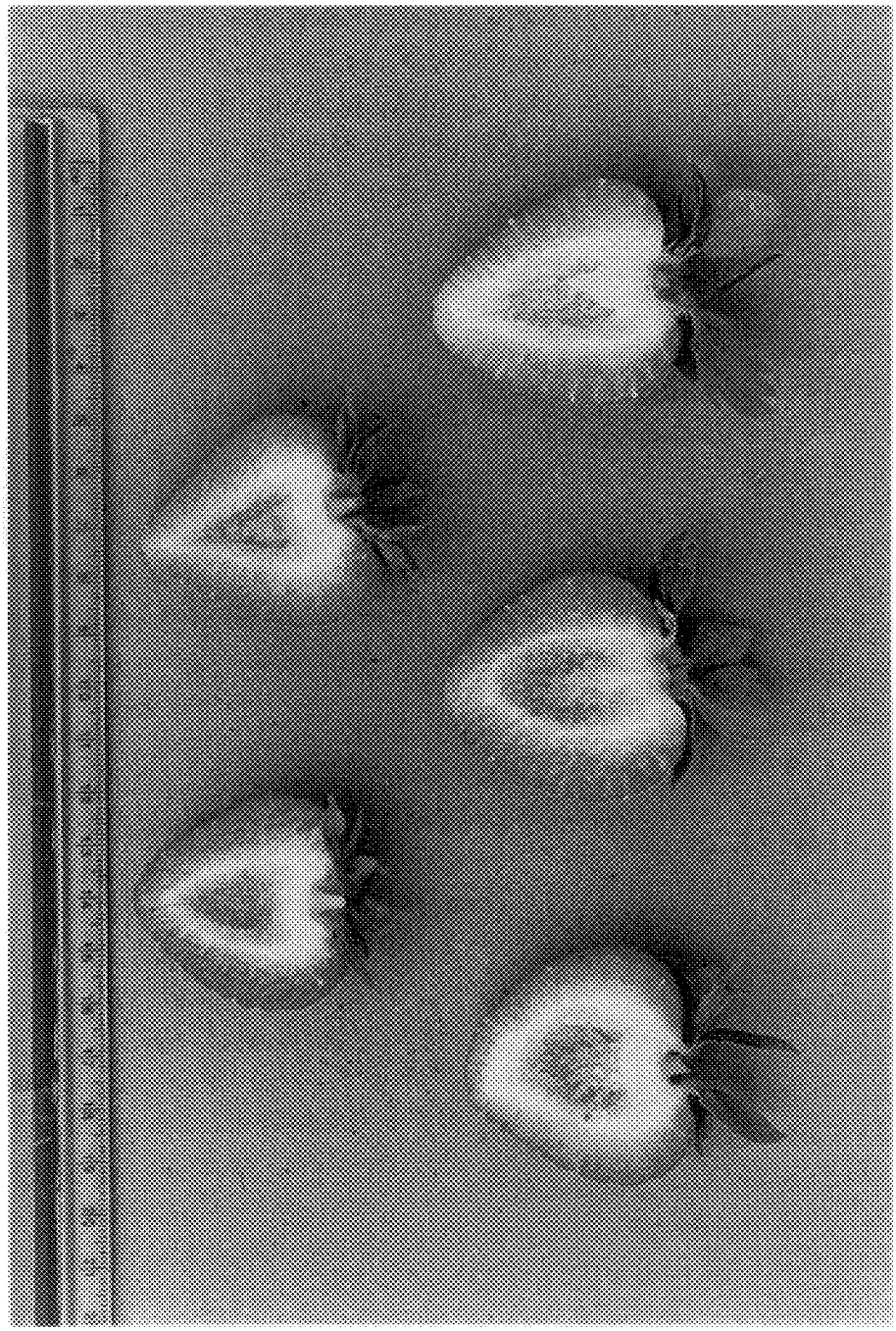
FIG. 4 shows the fruit in longitudinal cross-section.

The following detailed description of the new variety is based upon observations taken of plants and fruit grown in Ventura County, Calif., U.S.A. This description is in accordance with UPOV terminology. Observations of 'Driscoll Venice', 'Coronado' and 'San Miguel' were taken in side by side comparison in the year 2001. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of stolons. Although propagation by stolons is presently preferred, other known methods of propagating strawberry plants may be employed.

CHARACTERISTICS OF THE NEW VARIETY

Information on the new variety is presented in Tables 1, 2, 3 and 4. In the tables, the flowers described are secondary flowers except where indicated. The petal color of 'Driscoll Venice' is white (155C in The R.H.S. Colour Chart). The fruit described is the secondary fruit on one-year-old plants. Fruit and flower measurements are an average of both primary and secondary fruit and flowers. The average stolon diameter at bract subtending the daughter plant is 2.88 mm. The number of propagules/nursery plant in 2002 was 71. The anthocyanin coloration of the stipules in the Fall of the year in nursery is light pink 43D (in The R.H.S. Colour Chart). The petiolule length is 5.32 mm and the petiolule color is 149A (in The R.H.S. Colour Chart). The leaf texture is blistered, the leaf margin is crenate, the leaf vein color is 149A (in The R.H.S. Colour Chart), and the leaf venation is pinate. The petal shape is ovate to rounded, the petal margin is entire, the petal number is 6, and the petal color of the upper and lower surface is white 155C (in The R.H.S. Colour Chart). The sepal color is 147A (in The R.H.S. Colour Chart) on the upper surface and 147C (in The R.H.S. Colour Chart) on the lower surface, the average sepal number is 11.33, average sepal length is 15.64 mm, and average sepal width is 8.51 mm. The average weight of achenes is 0.00055 g and the average number of achenes/berry is 278.3. The anthocyanin color of stolon is purple red 59D (in The R.H.S. Colour Chart). The color of anthers is yellow 13A (in The R.H.S. Colour Chart) and the color of pistils and receptical is yellow 7A (in The R.H.S. Colour Chart).

Table 1 provides information on the plant and fruit characteristics of the new variety 'Driscoll Venice' compared with characteristics of 'Coronado' and 'San Miguel'. Table 2 provides additional information of the plant and fruit characteristics of the new variety 'Driscoll Venice' compared with characteristics of the varieties 'Coronado' and 'San Miguel'. Table 3 provides reactions of the new variety to stresses, pests and diseases compared with reactions of the varieties 'Coronado' and 'San Miguel'. Table 4 provides isozyme characteristics of the new variety as compared to that of the varieties 'Coronado' and 'San Miguel'.

TABLE 1

DETAILED COMPARISON OF 'DRISCOLL VENICE', 'CORONADO' AND 'SAN MIGUEL'

| | 'Driscoll Venice' | 'Coronado' | 'San Miguel' |
|---|---|---|---|
| Plant Characteristics | | | |
| Height of Plant (cm) | 19.5 | 20.7 | 22.8 |
| Spread of Plant (cm) | 26.0 | 28.7 | 29.4 |
| Number of Crowns | 3.4 | 4.6 | 4.4 |
| Leaf Characteristics | | | |
| Terminal Leaflet Length (cm) | 5.6 | 6.1 | 6.2 |
| Terminal Leaflet Width (cm) | 6.2 | 6.3 | 5.8 |
| Terminal Leaflet Length/Width | 0.91 | 0.97 | 1.07 |
| # Teeth/Terminal Leaflet | 22.7 | 21.6 | 20.7 |
| Color of upper side | dark green 147A | light to medium green 137A | medium to dark green 147A |
| Color of under side | light to medium green 139C | light to medium green 137B | light to medium green 138B |

TABLE 1-continued

DETAILED COMPARISON OF 'DRISCOLL VENICE', 'CORONADO' AND 'SAN MIGUEL'

| | 'Driscoll Venice' | 'Coronado' | 'San Miguel' |
|---|---|---|---|
| Petiole Length (cm) | 14.9 | 16.3 | 16.0 |
| Petiole Color | 149A | 149A | 149A |
| Bract Frequency | 0% | 0% | 25% typically paired |
| Stipule Length (cm) | 2.9 | 3.4 | 2.9 |
| Stipule Width (cm) | 1.0 | 1.2 | 1.1 |
| Flower Characteristics | | | |
| Petal Length (cm) | 1.7 | 1.6 | 1.4 |
| Petal Width (cm) | 1.6 | 1.7 | 1.5 |
| Petal Length/Width Ratio | 1.06 | 0.93 | 0.98 |
| Flower Diameter (cm) | 3.2 | 3.4 | 2.7 |
| Calyx Diameter (cm) | 4.4 | 4.4 | 4.1 |
| Fruiting Truss | | | |
| Length (cm) | 21.8 | 22.1 | 25.7 |
| Fruit Characteristics | | | |
| Fruit Length (cm) | 4.2 | 4.3 | 4.3 |
| Fruit Width (cm) | 4.1 | 3.9 | 4.1 |
| Fruit Length/Width Ratio | 1.04 | 1.11 | 1.07 |
| Average Berry Weight (g) | 27.0 | 23.6 | 23.2 |
| External Color | 45A | 46A | 53A |
| Internal Color | orange red and white (34A and 155C) | red 41A | dark red 45A |
| Average % brix | 8.1 | 7.1 | 7.1 |
| Brix/Acid Ratio | 10.75 | 9.11 | 9.33 |
| Achene Coloration | 60A to 15B | 53A to 151B | 53A to 14B |
| Yield (g/plant) | 695 | 598 | 557 |

TABLE 2

CHARACTERISTICS OF 'DRISCOLL VENICE', 'CORONADO' AND 'SAN MIGUEL'

| | 'Driscoll Venice' | 'Coronado' | 'San Miguel' |
|---|---|---|---|
| Plant | | | |
| Habit | globose | globose | flat globose |
| Density | dense | open | open |
| Vigor | medium | medium | medium |
| Leaf | | | |
| Shape in cross section | slightly concave | slightly concave | concave |
| Interveinal blistering | strong | strong | strong |
| Glossiness | strong | strong | strong |
| Number of leaflets | more than three on at least 5 out of 10 leaves | more than three on up to 5 out of 10 leaves | three only |
| Terminal leaflet margin profile | flat | flat to cupped | flat to revolute |
| Terminal leaflet shape of base | rounded | obtuse | rounded |
| Terminal leaflet shape of teeth | obtuse | rounded | rounded |
| Stipule pubescence | sparse to medium | sparse | sparse |
| Petiole pubescence | dense | medium | sparse to medium |
| Petiole pose of hairs | outward to downward | outward | outward |

TABLE 2-continued

CHARACTERISTICS OF 'DRISCOLL VENICE', 'CORONADO' AND 'SAN MIGUEL'

| | 'Driscoll Venice' | 'Coronado' | 'San Miguel' |
|---|---|---|---|
| Stolon | | | |
| Amount | many | medium to many | many |
| Anthocyanin coloration | medium | weak to medium | weak to medium |
| Thickness | medium | medium | thin to medium |
| Pubescence | medium to dense | sparse to medium | sparse to medium |
| Inflorescence | | | |
| Position relative to foliage | level to above | level to above | above |
| Diameter of calyx relative to corolla on secondary flowers | larger | larger | larger |
| Diameter of inner calyx relative to outer on secondary flowers | smaller | same size to larger | same size |
| Spacing of petals | touching to overlapping | touching to overlapping | overlapping |
| Fruiting Truss | | | |
| Attitude at first picking | prostrate | semi-erect to prostrate | prostrate |
| Fruit | | | |
| Predominant shape | cordate | conical to wedged | conical to cylindrical |
| Difference in shapes between primary and secondary fruits | slight | moderate | moderate |
| Band without achenes | very narrow | narrow | very narrow |
| Unevenness of surface | weak | weak to medium | weak to medium |
| Evenness of color uneven | slightly uneven to even | even | even |
| Glossiness | medium to strong | medium to strong | medium |
| Insertion of achenes | level with the surface | below surface | below surface |
| Insertion of calyx | level to set above | level to set above | set above |
| Pose of the calyx segments | reflexed | spreading | spreading to reflexed |
| Size of calyx in relation to fruit on secondary fruit | same size to larger | larger | same size |
| Adherence of calyx | strong | medium | strong |
| Firmness of flesh | medium | firm | firm |
| Evenness of flesh color | uneven | slightly uneven | even |
| Distribution of flesh color | only marginal | marginal and central | marginal and central |
| Hollow center size | small to medium | medium | medium |
| Sweetness | strong | weak | strong |
| Texture when tasted | fine | fine | fine |
| Acidity | weak | strong | medium |
| Time of Flowering | early-January | early-January | early-January |
| Harvest Interval in 2001 | early-February to mid-June | early-February to mid-June | early-February to mid-June |
| Type of Bearing | partially everbearing | partially everbearing | partially everbearing |

REACTION TO STRESS, PESTS AND DISEASE FOR 'DRISCOLL VENICE', 'CORONADO' AND 'SAN MIGUEL'

TABLE 3

| | 'Driscoll Venice' | 'Coronado' | 'San Miguel' |
|---|---|---|---|
| Reaction to Stress | | | |
| high pH | moderately resistant | moderately resistant | moderately resistant |
| high soil salt levels | moderately resistant | moderately resistant | moderately resistant |
| Reaction to Pests | | | |
| *Tetranychus urticae* | moderately resistant | moderately resistant | moderately resistant |
| *Lygus hesperus* | susceptible | susceptible | susceptible |
| Reaction To Diseases | | | |
| Botrytis fruit rot | moderately susceptible | moderately susceptible | moderately susceptible |
| Powdery mildew | moderately resistant | moderately resistant | moderately resistant |
| Verticillium wilt | susceptible | susceptible | susceptible |
| Strawberry Mottle Virus | moderately resistant | moderately resistant | moderately resistant |
| *Xanthomonas fragariae* | moderately susceptible | moderately susceptible | moderately susceptible |

ISOZYME ANALYSIS

In Addition to the Morphological Description Above, the New Cultivar 'Driscoll Venice' has been analyzed to obtain an indication of its genetic makeup to provide further means for identifying the new variety and distinguishing it from other somewhat similar and/or related strawberry varieties. Specifically, leaf samples of 'Driscoll Venice', 'Coronado', and 'San Miguel' were analyzed by electrophoresis for isozyme patterns of the enzymes phosphoglucoisomerase ("PGI"), leucine aminopeptidase ("LAP") and phosphoglucomutase ("PGM"). See *J. Amer. Soc. Hort. Sci.* 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL VENICE', 'CORONADO' AND 'SAN MIGUEL'

| Locus | 'Driscoll Venice' | 'Coronado' | 'San Miguel' |
|---|---|---|---|
| PGI | A4 | A2 | A4 |
| LAP | B3 | B3 | B3 |
| PGM | C2 | C4 | C2 |

What is claimed is:

1. A new and distinct variety of strawberry plant, substantially as shown and described.

* * * * *